(12) United States Patent
Garcia et al.

(10) Patent No.: US 10,799,394 B2
(45) Date of Patent: Oct. 13, 2020

(54) PATIENT INTERFACE DEVICE FOR LASER EYE SURGERY HAVING LIGHT GUIDING STRUCTURE FOR ILLUMINATING EYE

(71) Applicant: AMO Development, LLC, Santa Ana, CA (US)

(72) Inventors: Jose L. Garcia, Fremont, CA (US); Roger W. Accurso, Pleasanton, CA (US)

(73) Assignee: AMO Development, LLC, Santa Ana, CA (US)

(*) Notice: Subject to any disclaimer, the term of this patent is extended or adjusted under 35 U.S.C. 154(b) by 167 days.

(21) Appl. No.: 15/479,613

(22) Filed: Apr. 5, 2017

(65) Prior Publication Data

US 2017/0281407 A1 Oct. 5, 2017

Related U.S. Application Data

(60) Provisional application No. 62/318,693, filed on Apr. 5, 2016.

(51) Int. Cl.
 *A61F 9/009* (2006.01)
 *A61B 3/14* (2006.01)
 *A61B 18/22* (2006.01)

(52) U.S. Cl.
 CPC .............. *A61F 9/009* (2013.01); *A61B 3/14* (2013.01); *A61B 18/22* (2013.01); *A61B 2018/2272* (2013.01)

(58) Field of Classification Search
 CPC A61F 9/009; A61B 3/14; A61B 18/22; A61B 2018/2272
 See application file for complete search history.

(56) References Cited

U.S. PATENT DOCUMENTS 5,651,783 A 7/1997 Reynard
6,254,595 B1 7/2001 Juhasz et al.
(Continued)

FOREIGN PATENT DOCUMENTS

AU 2015202338 A1 5/2015
EP 1159986 A2 12/2001
(Continued)

OTHER PUBLICATIONS

Agilent Technologies, "Light Guide Techniques Using LED Lamps Application Brief I-003", http://www-eng.lbl.gov/~shuman/XENON/REFERENCES&OTHER_MISC/Lightpipe%20design.pdf, dated Dec. 7, 2001, viewed on Nov. 23, 2019.*
(Continued)

*Primary Examiner* — Christopher Koharski
*Assistant Examiner* — James Moss
(74) *Attorney, Agent, or Firm* — Johnson & Johnson Surgical Vision, Inc.

(57) ABSTRACT

A patient interface device includes: a first interface port configured to be interfaced with a laser surgery apparatus; a second interface port configured to be interfaced with a patient's eye, the second interface port including an applanating lens for application to a patient's eye during a laser surgery procedure; a chamber extending between the first interface port and the second interface port and defining a chamber therein, wherein air may be evacuated from the chamber by the laser surgery apparatus via the first interface port; and a tubular light guiding structure having at a first end thereof a light receiving surface, configured to receive light, and having at a second end thereof a light-emitting surface, wherein the second surface is disposed adjacent the applanating lens and configured to provide the light in a vicinity of the patient's eye when the applanating lens is applied to the patient's eye.

17 Claims, 12 Drawing Sheets

(56) References Cited

U.S. PATENT DOCUMENTS

| | | | |
|---|---|---|---|
| 6,344,040 B1 | 2/2002 | Juhasz et al. | |
| 6,373,571 B1 | 4/2002 | Juhasz et al. | |
| 6,623,476 B2 | 9/2003 | Kurtz et al. | |
| 6,863,667 B2 | 3/2005 | Webb et al. | |
| 6,899,707 B2 | 5/2005 | Scholler et al. | |
| 6,991,629 B1 | 1/2006 | Juhasz et al. | |
| 8,425,494 B2* | 4/2013 | Muhlhoff | A61F 9/009 414/751.1 |
| 8,469,952 B2* | 6/2013 | Muller | A61B 18/14 606/41 |
| 8,568,394 B2 | 10/2013 | Lummis et al. | |
| 8,740,890 B2 | 6/2014 | Vogler | |
| 8,753,321 B2 | 6/2014 | Mrochen et al. | |
| 8,845,624 B2 | 9/2014 | Raksi et al. | |
| 8,852,177 B2 | 10/2014 | Raksi | |
| 8,944,601 B2 | 2/2015 | Muehlhoff et al. | |
| 9,025,727 B2 | 5/2015 | Gertner et al. | |
| 9,066,784 B2 | 6/2015 | Goldshleger et al. | |
| 2001/0021844 A1* | 9/2001 | Kurtz | A61F 9/009 606/5 |
| 2007/0010804 A1* | 1/2007 | Rathjen | A61F 9/008 606/5 |
| 2007/0093795 A1* | 4/2007 | Melcher | A61F 9/009 606/10 |
| 2007/0179478 A1 | 8/2007 | Dobschal et al. | |
| 2008/0183159 A1* | 7/2008 | Preuss | A61F 9/00827 606/4 |
| 2010/0228236 A1* | 9/2010 | Muhlhoff | A61F 9/00827 606/4 |
| 2011/0190741 A1 | 8/2011 | Deisinger et al. | |
| 2013/0035674 A1* | 2/2013 | Lummis | A61F 9/009 606/5 |
| 2013/0226160 A1* | 8/2013 | Rathjen | A61F 9/00825 606/4 |
| 2014/0107634 A1 | 4/2014 | Vogler et al. | |
| 2014/0114296 A1 | 4/2014 | Woodley et al. | |
| 2014/0128821 A1* | 5/2014 | Gooding | A61F 9/009 604/290 |
| 2014/0216468 A1 | 8/2014 | Goldshleger et al. | |
| 2014/0222050 A1* | 8/2014 | Heitel | A61F 9/009 606/166 |
| 2014/0276673 A1 | 9/2014 | Heitel et al. | |
| 2014/0276674 A1 | 9/2014 | Lee et al. | |
| 2014/0276677 A1 | 9/2014 | Brownell et al. | |
| 2014/0364744 A1 | 12/2014 | Wellhoefer | |
| 2015/0190278 A1 | 7/2015 | Gooding et al. | |

FOREIGN PATENT DOCUMENTS

| | | |
|---|---|---|
| EP | 1570822 A1 | 9/2005 |
| EP | 1891915 A1 | 2/2008 |
| EP | 2913036 A1 | 9/2015 |
| WO | 2005048896 A1 | 6/2005 |
| WO | 2006090217 A1 | 8/2006 |
| WO | 2015119892 A1 | 8/2015 |

OTHER PUBLICATIONS

Lambda Research Corporation, "Designing and Optimizing Lightguides/Pipes", https://www.lambdares.com/wp-content/uploads/support/tracepro/tracepro_webinars/LED%20Professional%20Designing%20Light%20Pipes%20and%20Guides%20051215.pdf, posted Dec. 15, 2005, viewed on Nov. 23, 2019.*

Hisashi Uno et al., "GI-core polymer parallel optical waveguide with high-loss, carbon-black-doped cladding for extra low inter-channel crosstalk," 2010 23rd Annual Meeting of the IEEE Photonics Society, Denver, CO, 2010, pp. 106-107.doi: 10.1109/PHOTONICS.2010.5698780 . viewed on Nov. 23, 2019.*

International Search Report and Written Opinion for Application No. PCT/US2017/026084, dated Jun. 30, 2017, 14 pages.

* cited by examiner

FIG. 13

PATIENT INTERFACE DEVICE FOR LASER EYE SURGERY HAVING LIGHT GUIDING STRUCTURE FOR ILLUMINATING EYE

RELATED APPLICATIONS

This application claims priority to, and the benefit of, under 35 U.S.C. § 119(e) of U.S. Provisional Appl. No. 62/318,693, filed Apr. 5, 2016, which is incorporated by reference herein in its entirety.

TECHNICAL FIELD

Embodiments of this invention pertain to laser eye surgery, and in particular to a patient interface device for docking a patient's eye to a laser surgery instrument during laser eye surgery, and more particularly such a patent interface device having a light guiding structure for illuminating the patient's eye.

BACKGROUND AND SUMMARY

Laser surgery has become an important technique for the treatment of vision problems. It is necessary to stabilize the patient's eye of a patient during laser surgery in a predetermined position relative to the focal point of the laser beam, by physically constraining eye movement with respect to the laser beam during such laser surgery.

Toward this end, a patient interface device is typically applied to a patient's eye prior to the surgery, and also attached to the laser surgery apparatus via mechanical means. The patient interface has a lens for contact to the cornea and may use a vacuum force or other mechanical means to stabilize the patient's eye during the surgical procedure.

In general, existing patient interface devices are comprises of multiple pieces, and it can be difficult to join all the pieces together to fix the position of the patient's eye with respect to the laser surgery apparatus, especially if one part is already in contact with the patient and the other part is connected to the laser surgery apparatus. Various kinds of connectors are employed to join the various parts, such as a twist-lock mechanism, a one-way slide, etc. However, the connection process typically requires the patient to comply with various commands by the physician or physician's assistant, which may be difficult because the patient is often nervous and under sedation.

As noted above, existing patient interface devices employ a vacuum force to affix the patient interface device to the patient's eye and stabilize it while a shell of the patient interface device is attached to the laser surgery apparatus. In existing patient interface devices, the vacuum force is created by a manual pump or syringe attached to the patient interface device via one or more (e.g., plastic) vacuum lines (e.g., tube(s) or hose(s)) of various lengths, or else it is created by the laser surgery apparatus and applied by one or more one or more vacuum lines or hoses connecting the patient interface device to the laser surgery apparatus. In that case, an extra step may be required for the physician or physician's assistant to connect the vacuum tube(s) or hose(s). Also, the vacuum line(s) may need to e repositioned at various times during the laser surgery procedure. In general, the use of such vacuum lines is often awkward and unwieldy.

Due to the nature of the laser surgery procedure, it is often required to maintain a high degree of parallelism between the laser objective lens of the laser surgery apparatus which directs the surgical laser beam to the patient's eye, and the lens in the patient interface device. Achieving and ensuring such a high degree of parallelism is further complicated when the patient interface device comprises two or more parts which must be fitted and connected together. High manufacturing tolerances may be required which can increase cost and complexity.

Furthermore, during the laser surgery procedure, it is often required to illuminate the surgical area of the patient's eye, for example to capture images of the surgical area of the patient's eye which may be displayed to the physician to assist him in performing the surgery. However existing patient interface devices make it difficult to reliably and precisely deliver a desired amount of light to the vicinity of the patient's eye. Often times glare from the illuminating light source can impede a clear view of the surgical area. Other times not enough light is delivered to the vicinity of the patient's eye, producing captured images of the surgical area which are overly dark and difficult to see.

Accordingly, it would be desirable to provide a patient interface device which can at least partially mitigate one or more of the issues discussed above.

In one aspect, the present invention provides a patient interface device, comprising: a housing defining a chamber within; a first interface port configured to be interfaced with a patient's eye, the first interface port being disposed at a first side of the housing and including an applanating lens for application to the patient's eye during a laser surgery procedure; a second interface port disposed at a second side of the housing and configured to be interfaced with a laser surgery apparatus, wherein air may be evacuated from the chamber by the laser surgery apparatus via the second interface port; and a light guiding structure having at a first end thereof a light receiving interface, configured to receive light, and having at a second end thereof a light-emitting interface, wherein the light-emitting interface is disposed adjacent the applanating lens and configured to provide the light in a vicinity of the patient's eye when the applanating lens is applied to the patient's eye.

In some embodiments, the light guiding structure is tubular and has a light blocking material applied to at least a portion of an interior surface thereof extending from the first end to the second end, and further has the light blocking material applied to at least a portion of an exterior surface thereof extending from the first end to the second end.

In some versions of these embodiments, the light blocking material comprises a reflective material.

In some versions of these embodiments, the light blocking material comprises a layer of opaque material.

In some embodiments, the light guiding structure has a shape of a hollow conical frustum.

In some embodiments, the light guiding structure comprises at least one optical fiber.

In some embodiments, further comprising a flexible membrane on which the applanating lens is provided.

In some versions of these embodiments, the applanating lens has formed therein a circumferential groove, and wherein the flexible membrane includes a portion extending into the circumferential groove of the applanating lens to fix the applanating lens to the flexible membrane.

In some versions of these embodiments, the flexible membrane has formed therein a plurality of support structures configured to support the flexible membrane on a sclera of the patient's eye when the applanating lens is applied to the patient's eye.

In some embodiments, the first interface port includes a plurality of channels configured for the laser surgery apparatus to apply a vacuum to the applanating lens via the chamber.

In some embodiments, the light guiding structure is configured to internally reflect light from walls thereof from the light receiving interface to the light-emitting interface.

In another aspect, the present invention provides a system, comprising a laser surgery apparatus and a patient interface device. The laser surgery apparatus comprises: a laser source, a lens assembly configured to direct laser light from the laser source to a target area of a patient's eye for laser surgery, a docking receptacle, and an illuminating light source. The patient interface device comprises: a shell defining a chamber within, a first interface port configured to be interfaced with the patient's eye, the first interface port being disposed at a first side of the shell and including an applanating lens for application to the patient's eye during a laser surgery procedure, a second interface port disposed at a second side of the shell and configured to be interfaced with the docking receptacle, wherein air may be evacuated from the chamber by the laser surgery apparatus via the second interface port, and a light guiding structure having at a first end thereof a light receiving interface, configured to receive light from the illuminating light source, and having at a second end thereof a light-emitting interface, wherein the light-emitting interface is disposed adjacent the applanating lens and configured to provide the light in a vicinity of the patient's eye when the applanating lens is applied to the patient's eye.

In some embodiments, the system further comprises an imaging device configured to produce image data for the patient's eye while the patient's eye is illuminated by the light from the light guiding structure.

In some embodiments, the light guiding structure is tubular and has a light blocking material applied to at least a portion of an interior surface thereof extending from the first end to the second end, and further has the light blocking material applied to at least a portion of an exterior surface thereof extending from the first end to the second end.

In some versions of these embodiments, the light blocking material comprises a reflective material.

In some versions of these embodiments, the light blocking material comprises a layer of opaque material.

In some embodiments, the light guiding structure has a shape of a hollow conical frustum.

In some embodiments, the light guiding structure comprises at least one optical fiber.

In some embodiments, further comprising a flexible membrane on which the applanating lens is provided.

In some versions of these embodiments, the applanating lens has formed therein a circumferential groove, and wherein the flexible membrane includes a portion extending into the circumferential groove of the applanating lens to fix the applanating lens to the flexible membrane.

In some embodiments, the first interface port includes a plurality of channels configured for the laser surgery apparatus to apply a vacuum to the applanating lens via the chamber.

In some embodiments, the light guiding structure is configured to internally reflect light from walls thereof from the light receiving interface to the light-emitting interface.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of laser surgery systems and eye stabilization devices are described below to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

Figure 1:
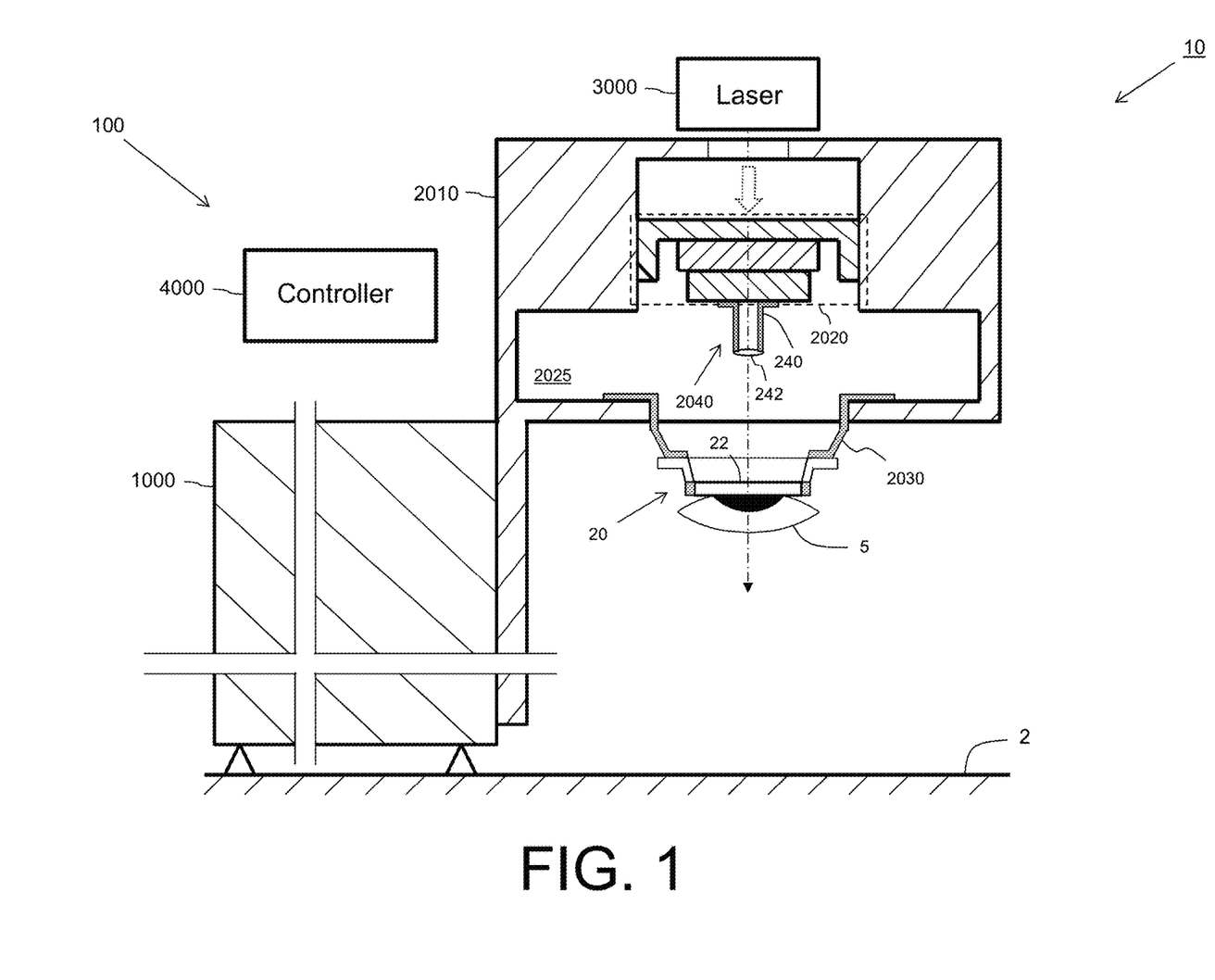
FIG. 1 illustrates an example embodiment of an arrangement of a laser surgery system and an eye stabilization device.

FIG. 1 illustrates an example embodiment of an arrangement 10 of a laser surgery apparatus 100 and an eye stabilization device.

Laser surgery apparatus 100 includes a structural frame or base 1000, a gantry 2010 movable in three dimensions and attached to the structural frame; an adjustable table 2020 attached to gantry 2010; a docking receptacle 2030; a lens assembly 2040 attached to adjustable table 2020; a laser 3000; and a controller 4000. Laser surgery apparatus 100 may include a number of other elements which are not shown in FIG. 1, and some elements in FIG. 1 which are not closely related to aspects of the present invention are not labeled so as not to obscure other significant details. Furthermore, in the interest of brevity, these elements will not be discussed here.

Here, the eye stabilization device comprises a patient interface device 20 including an applanating lens 22. Patient interface device 20 is configured to be docked or connected to docking receptacle 2030 to form a patient interface for laser surgery. Beneficially, patient interface 20 is a single-use disposable element which is attached to a subject's eye, or patient's eye, 5 in advance of laser surgery. In some embodiments, as will be discussed in greater detail below, laser surgery apparatus 100 may also include a vacuum pump (not shown) mounted within laser surgery system 100 for applying a vacuum to the interior of patient interface device 20 via docking receptacle 2020 and an interior region or chamber of 2025 of laser surgery apparatus 100.

FIG. 1 is a sort of "hybrid" illustration which illustrates certain structural elements such as structural frame 1000, gantry 2010, adjustable table 2020, docking receptacle 2030, lens assembly 2040, and eye docking assembly 20 cross-sectionally, and which shows other elements such as laser 3000 and controller 4000 as functional blocks.

Lens assembly 2040 includes a lens 242 and an optical structure 240 holding lens 242 and providing an optical path for laser light from laser 3000 to pass through lens assembly 2040, and specifically to pass through lens 240.

Controller 4000 may include one or more processors and associated memory (e.g., random access memory (RAM), FLASH memory, read only memory (ROM), etc.) which may store therein computer-readable instructions for one or more algorithms to be executed by the processor(s) of controller 4000.

Gantry 2010 is attached the structural frame 1000 and adjustable table 2020 is attached to gantry 2010. Controller 4000 may control movement of adjustable table 2020.

In some embodiments, laser 3000 may be provided as a separate device, apart from the rest of laser surgery apparatus 100. In some embodiments, structural frame 1000 may be provided as a separate element to which the rest of laser surgery apparatus 100 is attached or connected.

Figure 2:
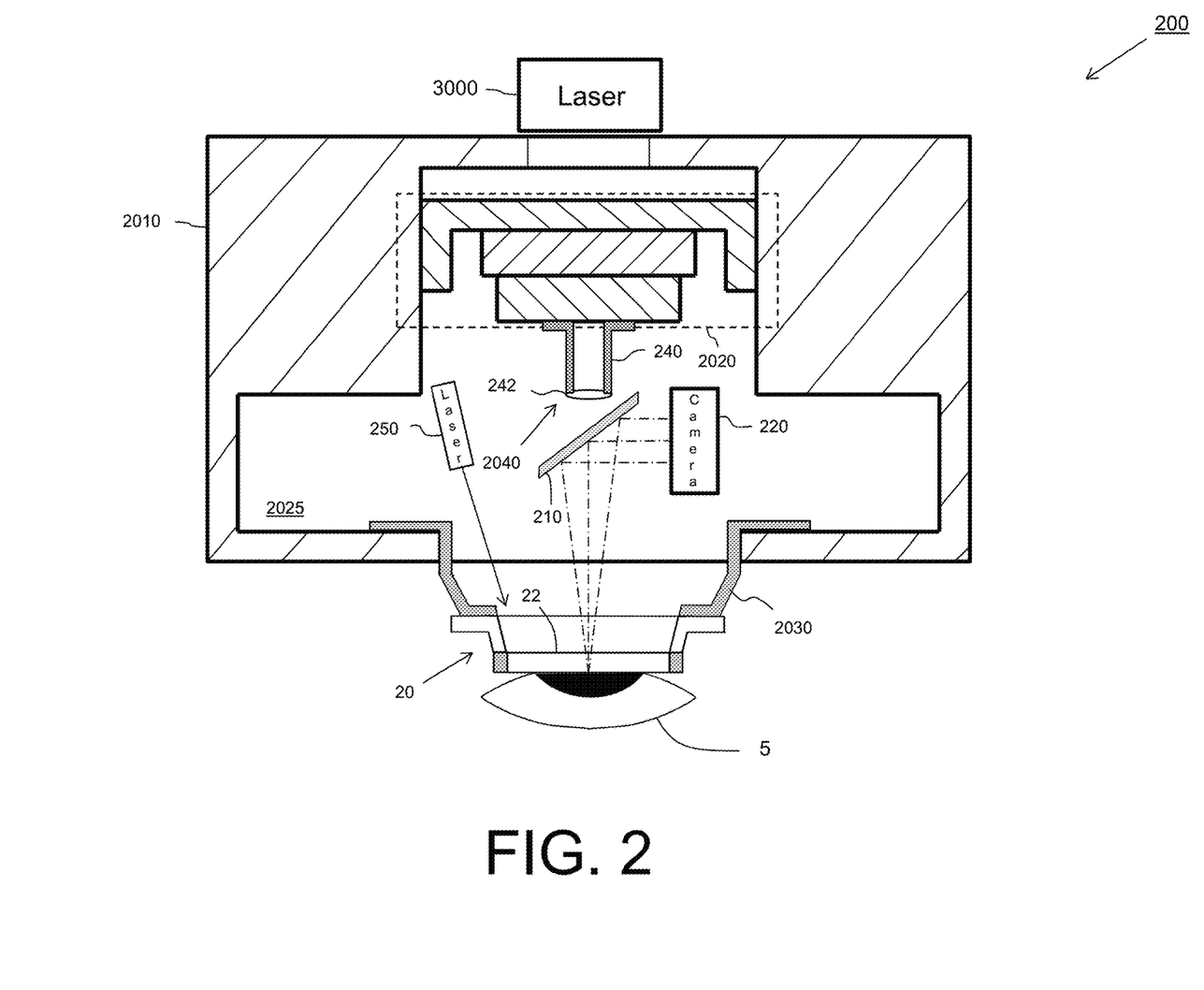
FIG. 2 illustrates an example of a portion of a laser surgery system which employs a camera for viewing an eye during a laser surgery procedure.

FIG. 2 illustrates an example of a portion of a laser surgery system which employs a camera in an eye docking procedure. Here, laser surgery apparatus 200 is a variation of laser surgery apparatus 100 and so a repeated description of the common elements between laser surgery apparatus 100 and laser surgery apparatus 200 will not be repeated.

Laser surgery apparatus 200 includes a mirror or beamsplitter 210 and an imaging device (e.g., a camera) 220. Here, beamsplitter 210 and an imaging device 220 may be configured to be removably inserted into between lens assembly 2040 and docking receptacle 2030, for example under the control of one or more motors (not shown), after adjustable table 2020 is moved far away from docking receptacle 2030. As will be described in greater detail below, in some embodiments imaging device 220 may produce image data for a patient's eye 5 and provide this image data to a user via a heads-up display and/or to controller 4000, wherein the image data may be used to control movement of gantry 2010 to dock patient interface 20 to docking receptacle 2030 during an eye docking procedure prior to the commencement of laser surgery on patient's eye 5.

Figure 3:
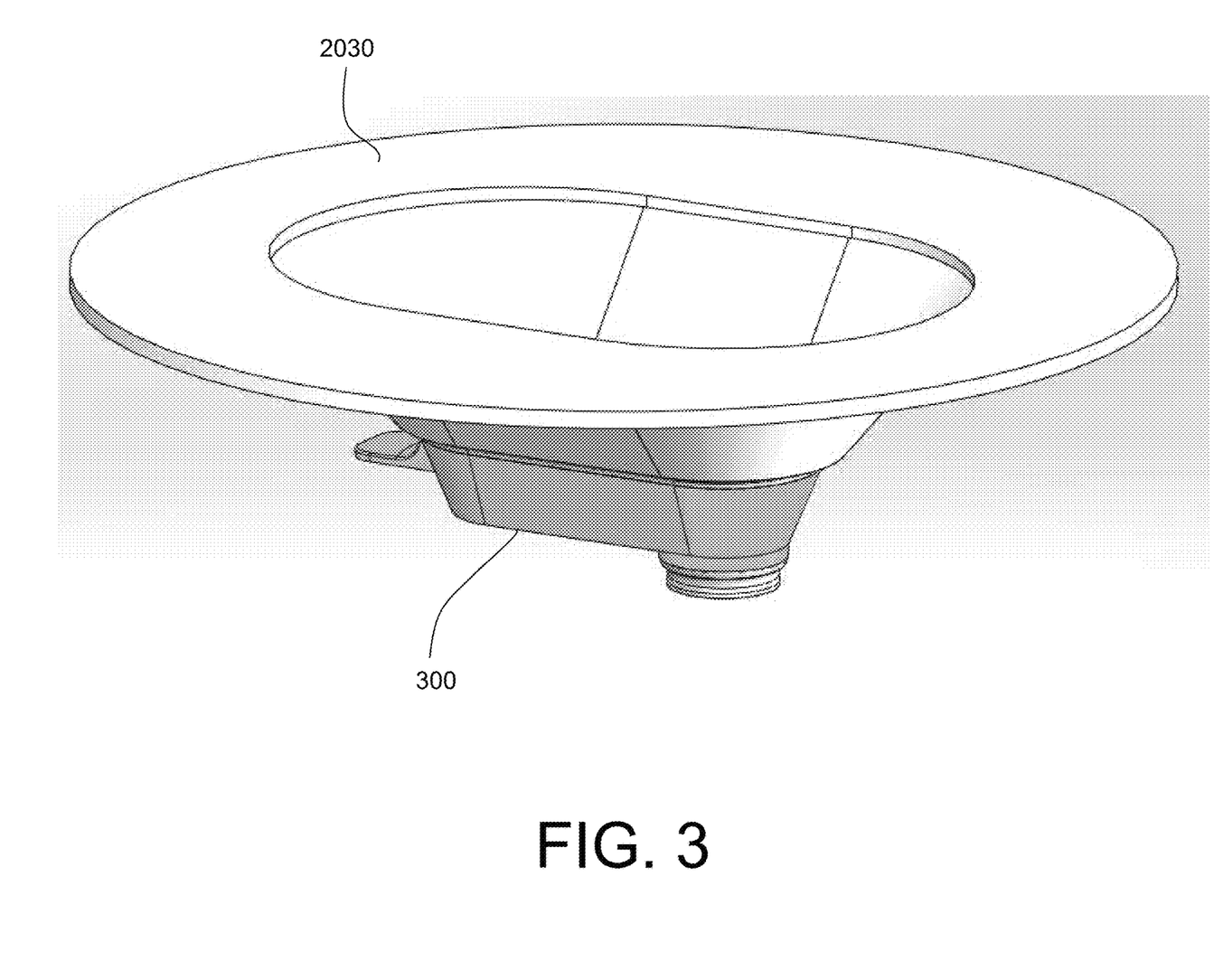
FIG. 3 illustrates an example embodiment of a docking receptacle and an example embodiment of a patient interface device.

FIG. 3 illustrates an example embodiment of a docking receptacle 2030 and an example embodiment of patient interface device 300. Patient interface device 300 may be one embodiment of patient interface device 20 of FIGS. 1 and 2.

Figure 4:
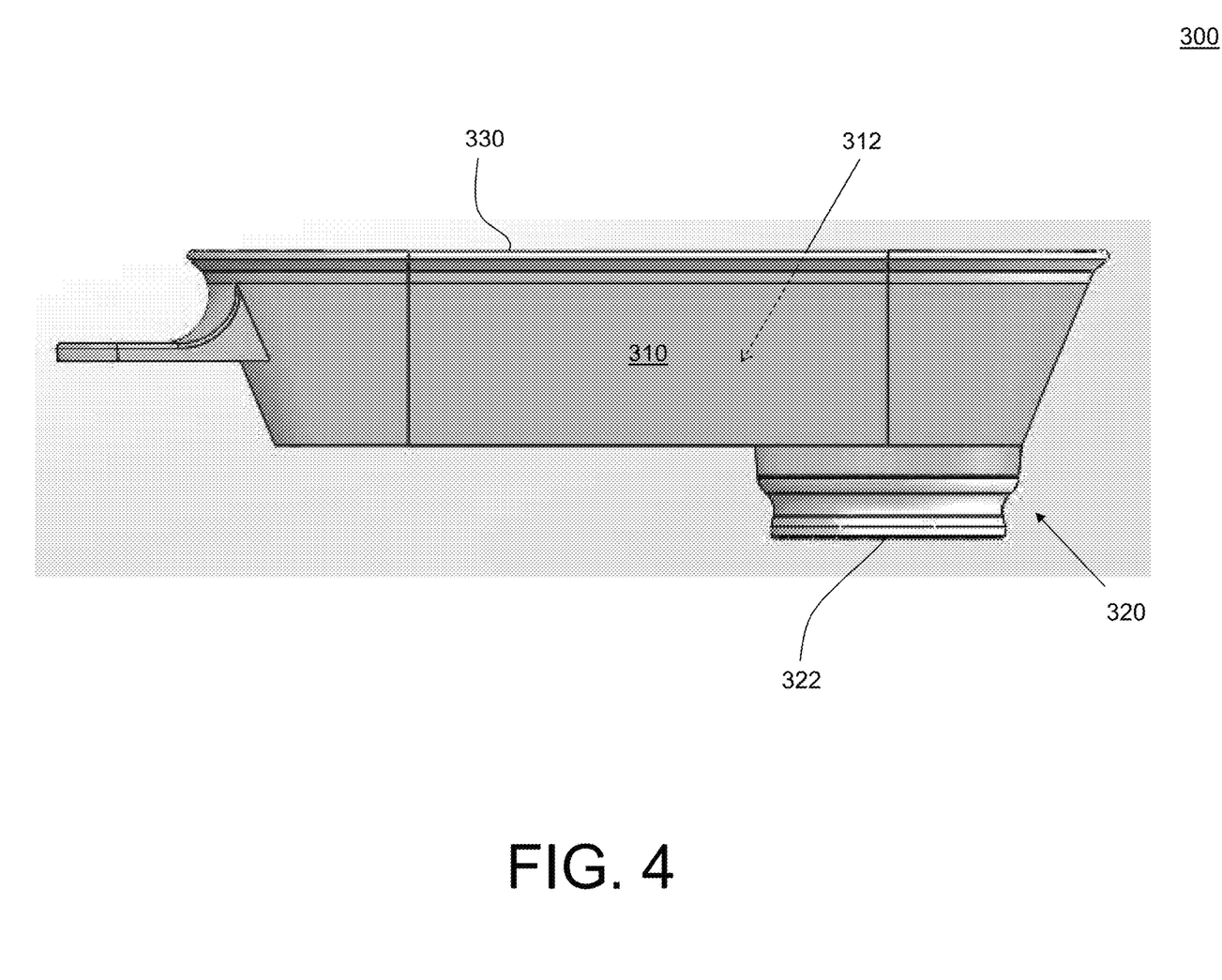
FIG. 4 illustrates an example embodiment of a patient interface device.

FIG. 4 illustrates in greater detail patient interface device 300. Patient interface device 300 comprises: a substantially hollow shell 310 defining a chamber or cavity 312 therein; a first interface port 320 configured to be interfaced with patient's eye 5; and a second interface port 330 disposed at a second side of shell 310. First interface port 320 is disposed at a first side of shell 310 and includes applanating lens 22 for application to patient's eye 5 during a laser surgery procedure. Second interface port 330 is configured to be interfaced with a laser surgery apparatus (e.g., laser surgery apparatus 100 or laser surgery apparatus 200) via docking receptacle 2030.

Beneficially, when patient interface device 300 is attached to the laser surgery apparatus, air may be evacuated from the chamber or interior cavity 312 of shell 310 via second interface port 330 by a pump of the laser surgery apparatus, for example through interior region 2025 of laser surgery apparatus 100 or laser surgery apparatus 200 and docking receptacle 2030. Therefore, beneficially patient interface device 300 does not include any vacuum lines or hoses, and instead the vacuum force is applied to applanating lens 22 via a pump of the laser surgery apparatus, for example through interior region 2025 of laser surgery apparatus 100 and the interior of docking receptacle 2030.

Beneficially, patient interface device 300 comprises a singular, integrated, unitary structure which can be attached to a docking receptacle (e.g., docking receptacle 2030) of a laser surgery apparatus (e.g., laser surgery apparatus 100 or laser surgery apparatus 200) via a mechanical feature that allows it to snap into place. Accordingly, assembly or connection of multiple pieces of a patient interface device for a laser surgery procedure may be avoided.

Figure 5:
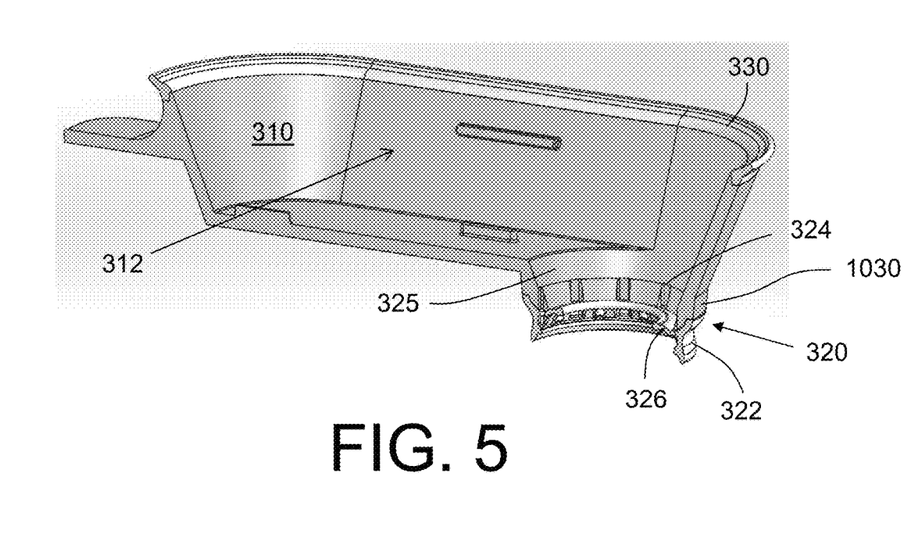
FIG. 5 shows a cutaway interior view of a portion of an example embodiment of a patient interface device.
Figure 7:
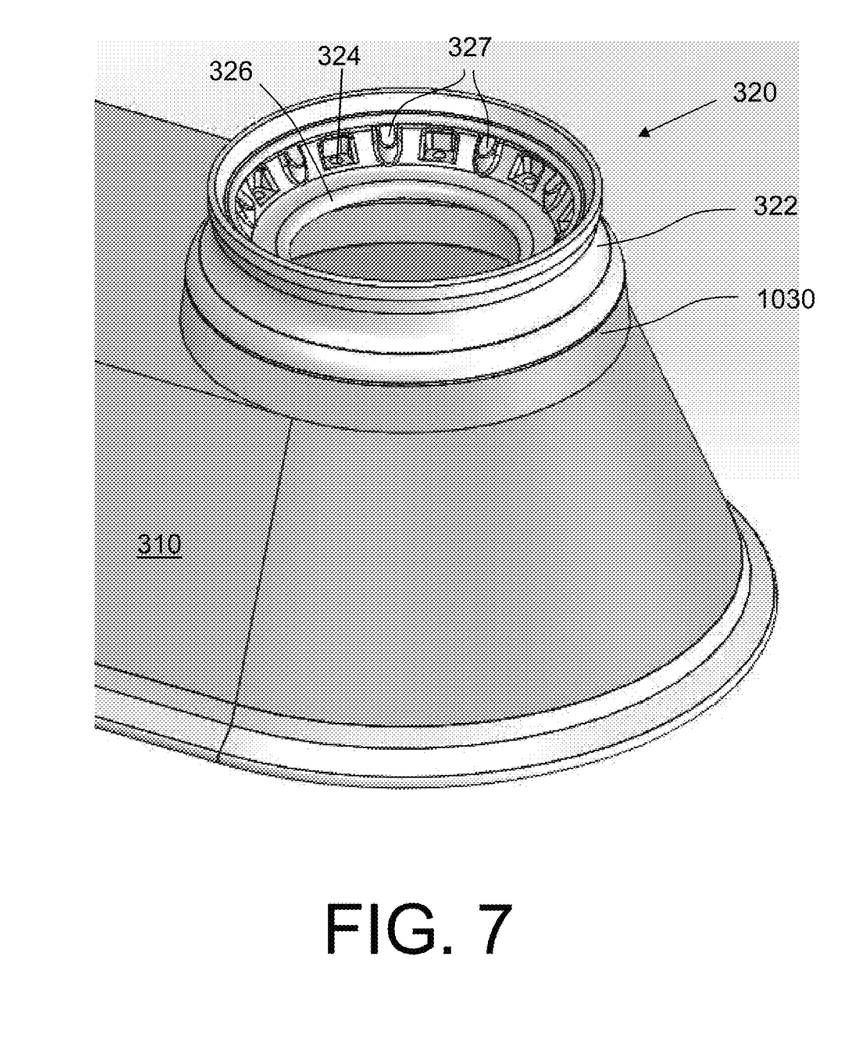
FIG. 7 shows another view of a portion of an example embodiment of a patient interface device.
Figure 8:
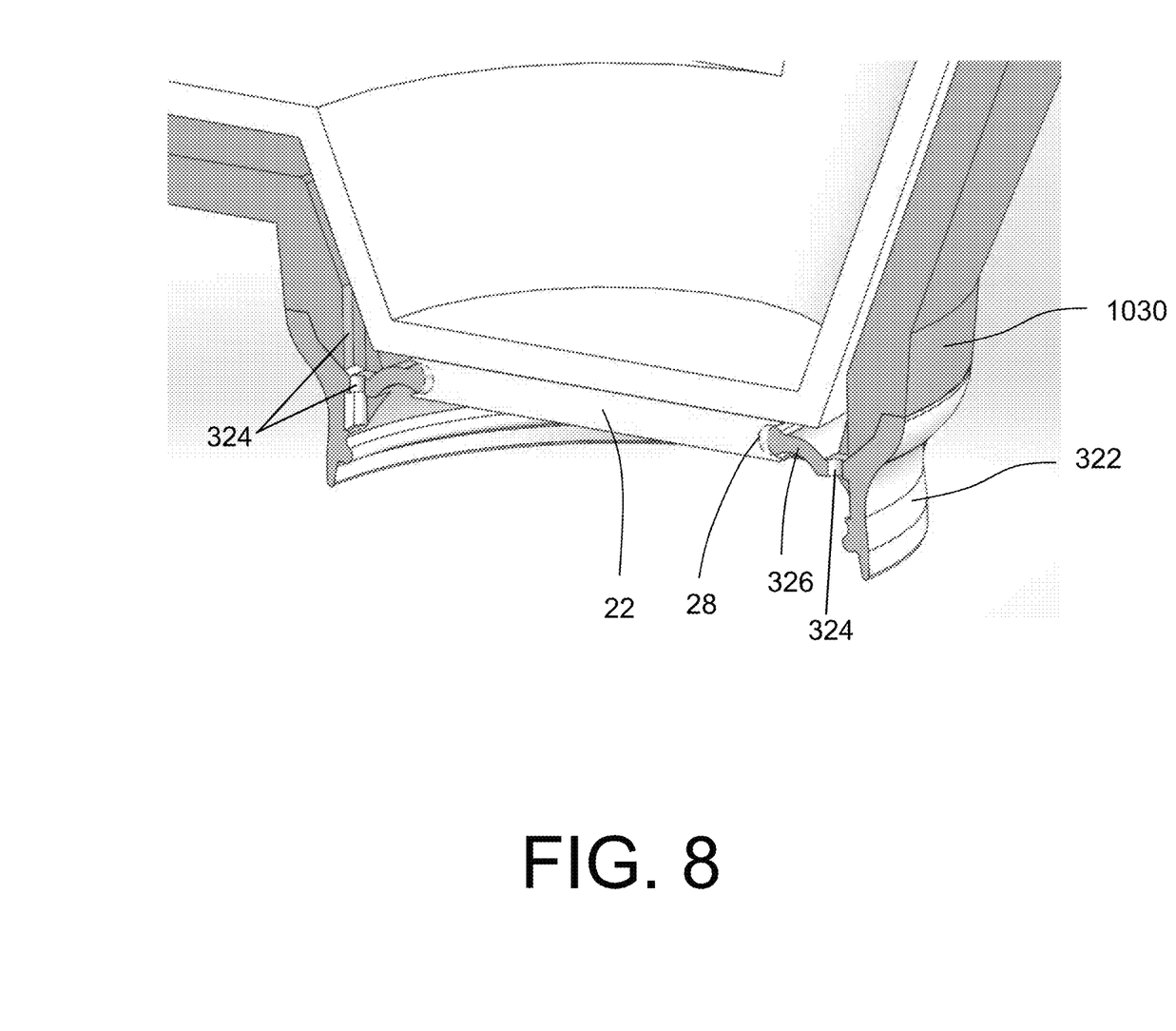
FIG. 8 shows yet another cutaway interior view of a portion of an example embodiment of a patient interface device, including an applanating lens.

FIG. 5 shows a cutaway interior view of a portion of patient interface device 300. In particular, FIG. 5 illustrates in greater detail features of first interface port 320, including a flexible or semi-flexible (e.g., rubber) membrane 322, a frustoconical portion 325 which may serve as a portion of a light guiding structure, as discussed in greater detail below, and a termination region 1030 which may serve as a light-emitting, or light-diffusing, interface or surface of such a light guiding structure. Also provided at first interface port 320 are a plurality of vacuum channels 324 configured for the laser surgery apparatus to apply a vacuum to applanating lens 22 via the interior chamber or cavity 312 of shell 310. As shown in FIGS. 7 and 8, the vacuum channels 324 extend through the membrane 322 from the space above the applanating lens 22 to the space below the applanating lens, which allow the vacuum pressure to be transmitted from the space above the applanating lens to the space below the applanating lens.

Figure 6:
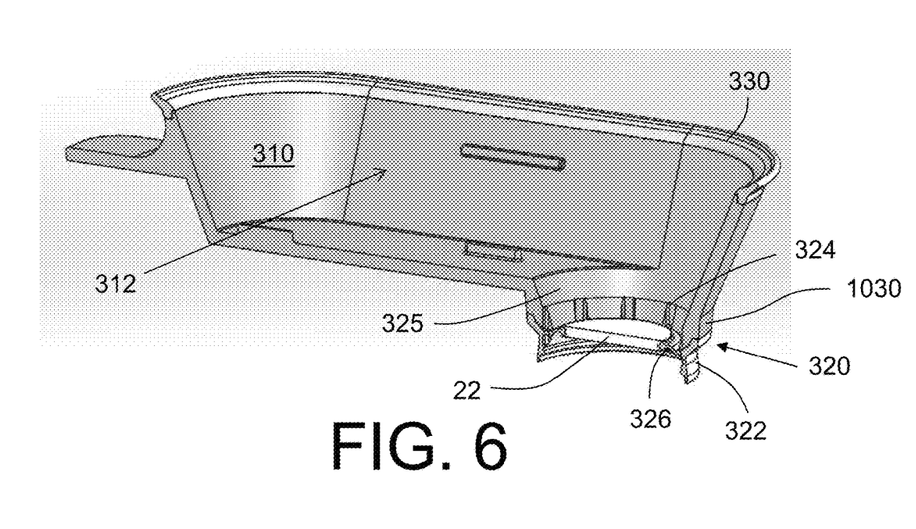
FIG. 6 shows another cutaway interior view of a portion of an example embodiment of a patient interface device, including an applanating lens.

FIG. 6 shows another cutaway interior view of a portion of an example embodiment of a patient interface device, similar to what is shown in FIG. 5, but also showing applanating lens 22.

FIG. 7 shows another view of first interface port 320 of patient interface device 300. Here, applanating lens 22 is removed for better view of various elements. In particular, FIG. 7 illustrates membrane 322 includes a portion 326 as a supporting or retaining ring which surrounds and supports applanating lens 22. In the illustrated embodiment, membrane 322 includes, or has formed therein, a plurality of support structures 327 configured to support membrane 322 on a sclera of patient's eye 5 when applanating lens 22 is applied to patient's eye 5.

FIG. 8 shows yet another cutaway interior view of first interface port 320 of patient interface device 300, including applanating lens 22. Here is more clearly seen that portion 326 of membrane 322 extends into a circumferential groove 28 of applanating lens 22 to fix applanating lens 22 to membrane 322. Beneficially, the portion 326 of membrane 322 extending into circumferential groove 28 of applanating lens 22 allows applanating lens 22 to confirm to and maintain parallelism between applanating lens and the focusing or objective lens (e.g., lens 242) of the laser surgery apparatus (e.g., laser surgery apparatus 100 or laser surgery apparatus 200).

Figure 9:
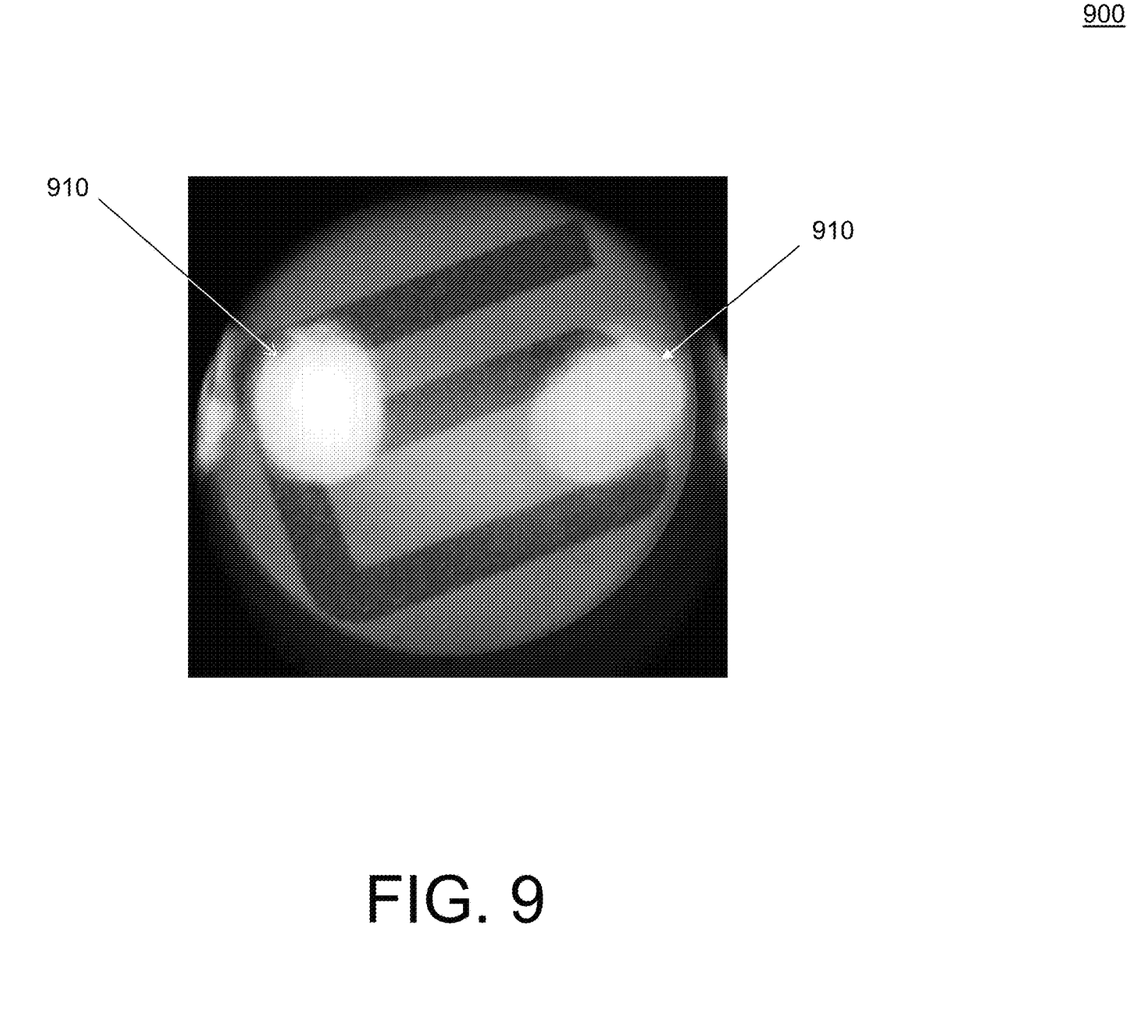
FIG. 9 illustrates a problem which may occur when attempting to generate an image of a patient's eye while the eye is attached to a patent interface device for a laser surgery apparatus.

FIG. 9 illustrates a problem which may occur when attempting to generate an image 900 of patient's eye 5 while patient's eye 5 is attached to a patent interface device for a laser surgery apparatus. In particular, image 900, which may be captured by a video camera (e.g., video camera 220) or other imaging device, shows a pair of "light hot spots" 910 from an illumination source for illuminating patient's eye 5. Light hot spits 910 may obscure a proper view of patient's eye 5 in the image 900 produced by the video camera. In other cases, not enough light is delivered to the vicinity of patient's eye 5 to allow the video camera or imaging device to capture a good image of patient's eye 5.

To address this issue and better illuminate a surgical area of patient's eye 5, beneficially a patient interface device (e.g., patient interface device 300) may be provided with a light guiding structure which is configured to receive light at a light receiving interface or surface, and to provide the light in a vicinity of patient's eye 5 when applanating lens 22 is applied to patient's eye 5 via a light-emitting interface or surface disposed adjacent the applanating lens. In some embodiments, the light guiding structure may couple the light from the light receiving interface or surface to the light-emitting interface or surface by total internal reflection.

Figure 10:
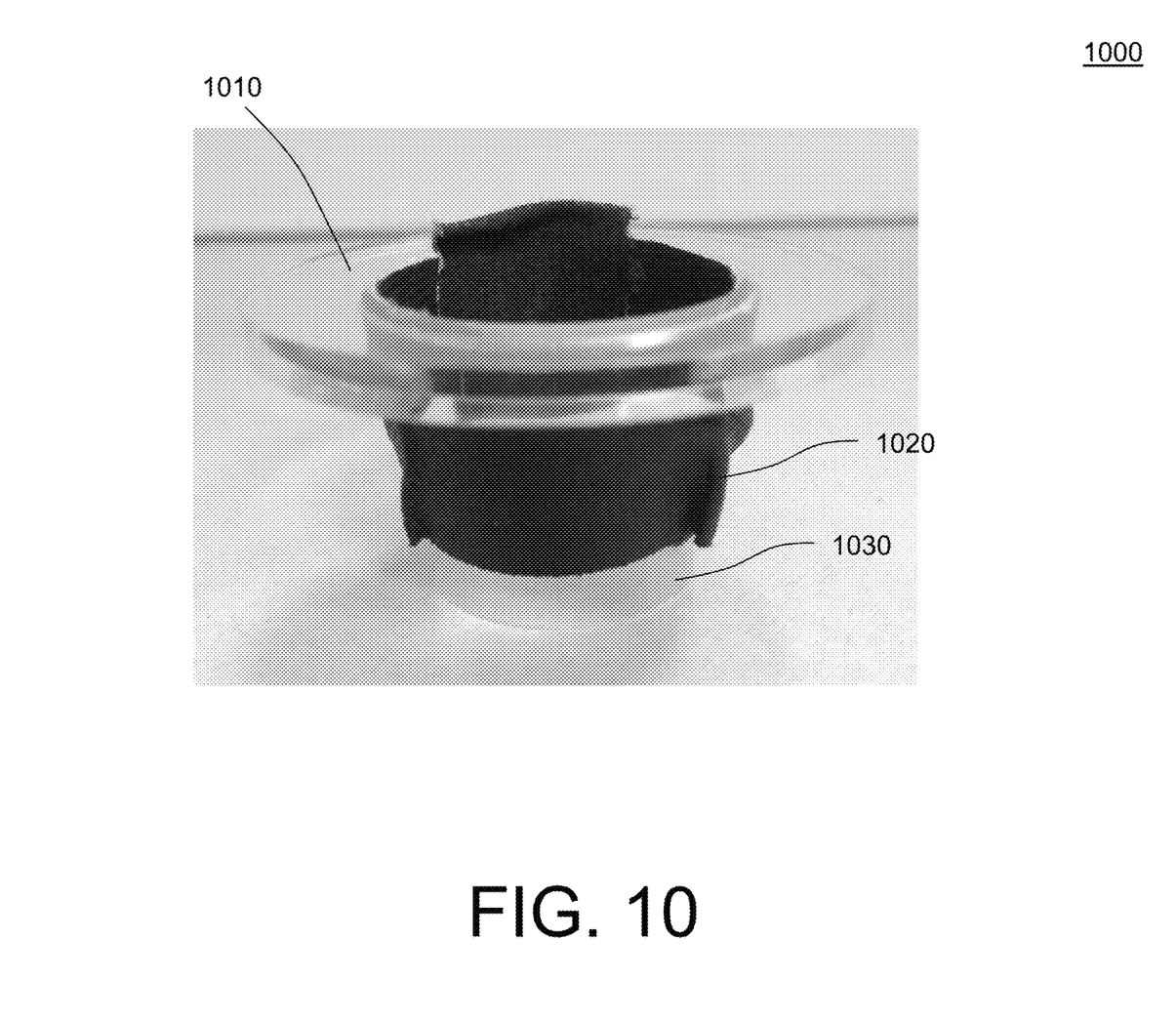
FIG. 10 illustrates an example embodiment of a light guiding structure of a patient interface device.

FIG. 10 illustrates an example embodiment of a light guiding structure 1000 of a patient interface device (e.g., patient interface device 300). Light guiding structure 1000 has at a first end thereof a light receiving interface 1010, configured to receive light, and further has at a second end thereof a light-emitting interface 1030. Here, in operation during a laser surgery procedure light-emitting interface 1030 is disposed adjacent applanating lens 22 and configured to provide the light in a vicinity of patient's eye 5 when applanating lens 22 is applied to patient's eye 5.

In some embodiments, light-emitting interface 1030 comprises a light diffusing surface for more evenly distributing the light in the vicinity of patient's eye 5.

Beneficially, light guiding structure 1000 comprises a material which is transparent to visible light, such as glass, polycarbonate, or acrylic (e.g., Polymethyl methacrylate (PMMA)). Beneficially, the surfaces of light guiding structure 1000 may be polished to a high degree, e.g., 2500 grit, except in some embodiments at light-emitting interface 1030 where a rougher, or non-polished, surface (e.g., 400 grit) may be provided to better diffuse the light.

Beneficially, light guiding structure 1000 is tubular or substantially tubular, with a hollow interior opening or channel where applanating lens 22 is disposed and via which a surgical laser beam may pass from a laser surgery apparatus (e.g., laser surgery apparatus 100 or laser surgery apparatus 200) through applanating lens 22 to patient's eye 5.

Beneficially, light guiding structure 1000 may have a light blocking material 1020 applied to at least a portion of an interior surface thereof extending from the first end to the second end, and further may have light blocking material 1020 applied to at least a portion of an exterior surface thereof extending from the first end to the second end. In some embodiments, light blocking material 1020 may comprise a layer or coating of an opaque material, such as black paint. Here, light blocking material 1020 comprises dark (e.g., black) tape. In other embodiments, light blocking material 1020 may comprise a reflective material layer or coating, for example a metal or mirror.

Figure 11A:
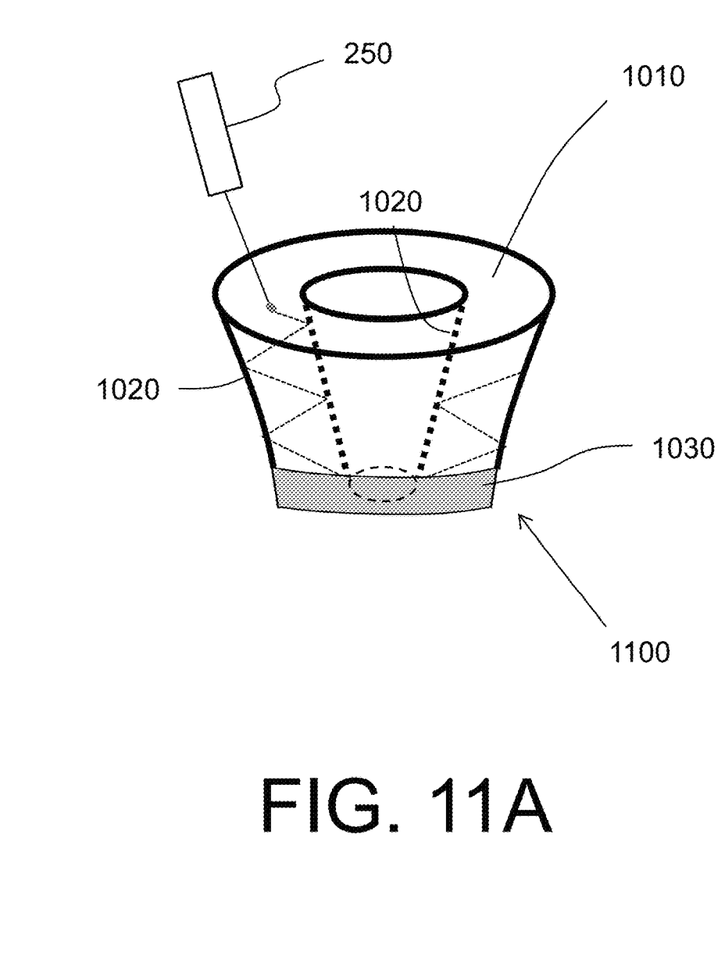
FIG. 11A illustrates a perspective view of another example embodiment of a light guiding structure of a patient interface device.
Figure 11B:
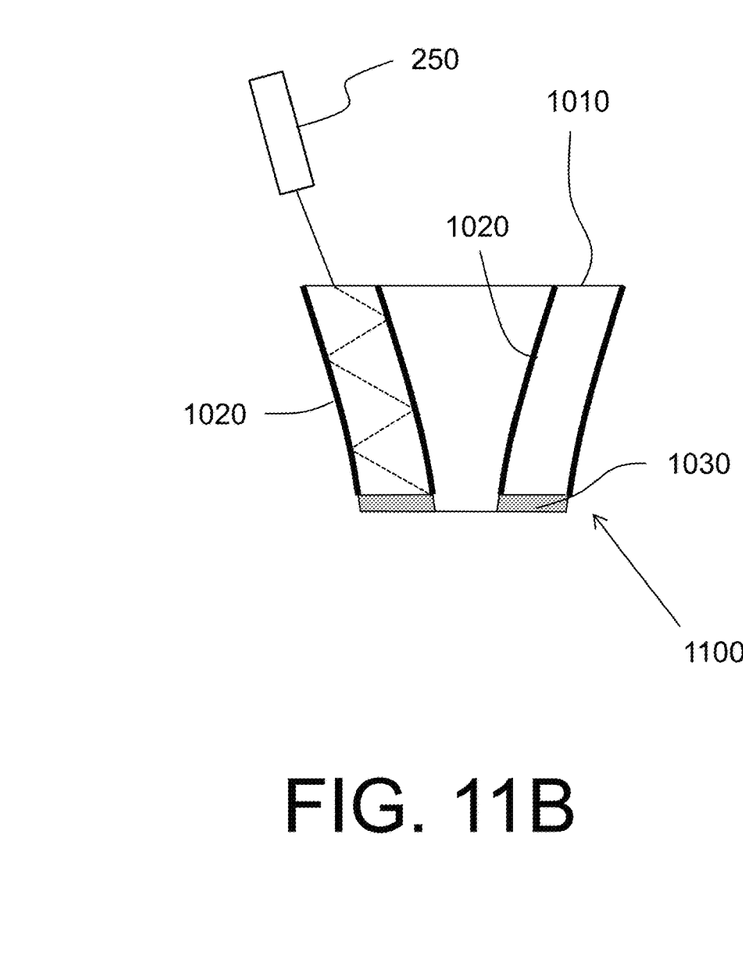
FIG. 11B illustrates a side view of the other example embodiment of the light guiding structure of a patient interface device.

FIG. 11A illustrates a perspective view of another example embodiment of a light guiding structure 1100 of a patient interface device (e.g., patient interface device 300), and FIG. 11B illustrates a side view of the other example embodiment of light guiding structure 1100 of a patient interface device.

Beneficially, light guiding structure 1100 comprises a material which is transparent to visible light, such as glass, polycarbonate, or acrylic (e.g., Polymethyl methacrylate (PMMA)). Beneficially, the surfaces of light guiding structure 1100 may be polished to a high degree, e.g., 2500 grit, except in some embodiments at light-emitting interface 1030 where rougher surface (e.g., 400 grit) may be provided to better diffuse the light.

Light guiding structure 1100 is in the shape of a hollow frustum of a cone. FIGS. 11A and 11B illustrate that light guiding structure 1100 has at a first end thereof light receiving interface 1010, configured to receive light, and further has at a second end thereof light-emitting interface 1030. Here, in operation during a laser surgery procedure light-emitting interface 1030 is disposed adjacent applanating lens 22 and configured to provide the light in a vicinity of patient's eye 5 when applanating lens 22 is applied to patient's eye 5. Beneficially, light guiding structure 1000 may have a light blocking material 1020 applied to at least a portion of an interior surface thereof extending from the first end to the second end, and further has light blocking material 1020 applied to at least a portion of an exterior surface thereof extending from the first end to the second end. Most of the light blocking material 1020 is removed in FIGS. 11A and 11B so as to better illustrate operation of light guiding structure 1100.

As shown in FIGS. 11A and 11B, an illumination source (e.g., a laser) 250 provides light to light receiving interface or surface 1010 of light guiding structure 1100. Light guiding structure 1100 couples the light via internal reflections (e.g., total internal reflection (TIR)) to light-emitting interface or surface 1030, near the location of applanating lens 22, where it is provided to the vicinity of patient's eye 5. In particular, illumination source 250 may emit light in a direction such that it is oriented at an angle with respect to light receiving interface or surface 1010 and the sidewalls of the substrate of the patient interface device (e.g., patient interface device 300) may be arranged or configured such that the patient interface device acts as an internal mirror to internally reflect the light toward the vicinity of patient's eye 5, without need for light blocking material 1020 (e.g., a mirror coating). Beneficially, light-emitting interface or surface 1030 may include a diffusing structure or surface so that the light is diffusely provided to the vicinity of patient's eye 5.

Figure 12A:
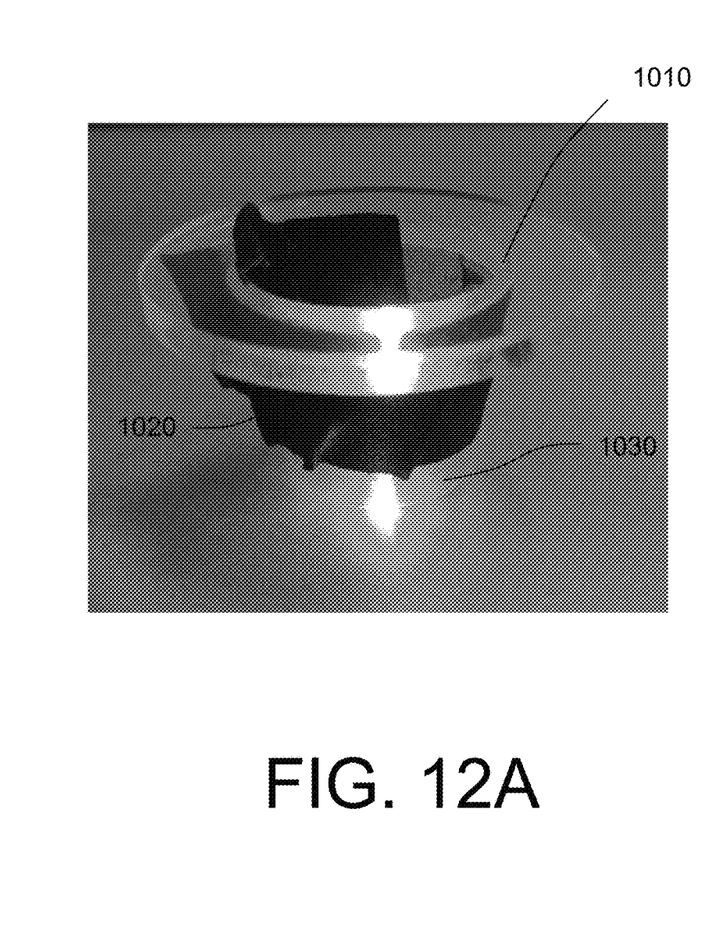
FIG. 12A illustrates a first example of an illumination condition of an example embodiment of a light guiding structure of a patient interface device.
Figure 12B:
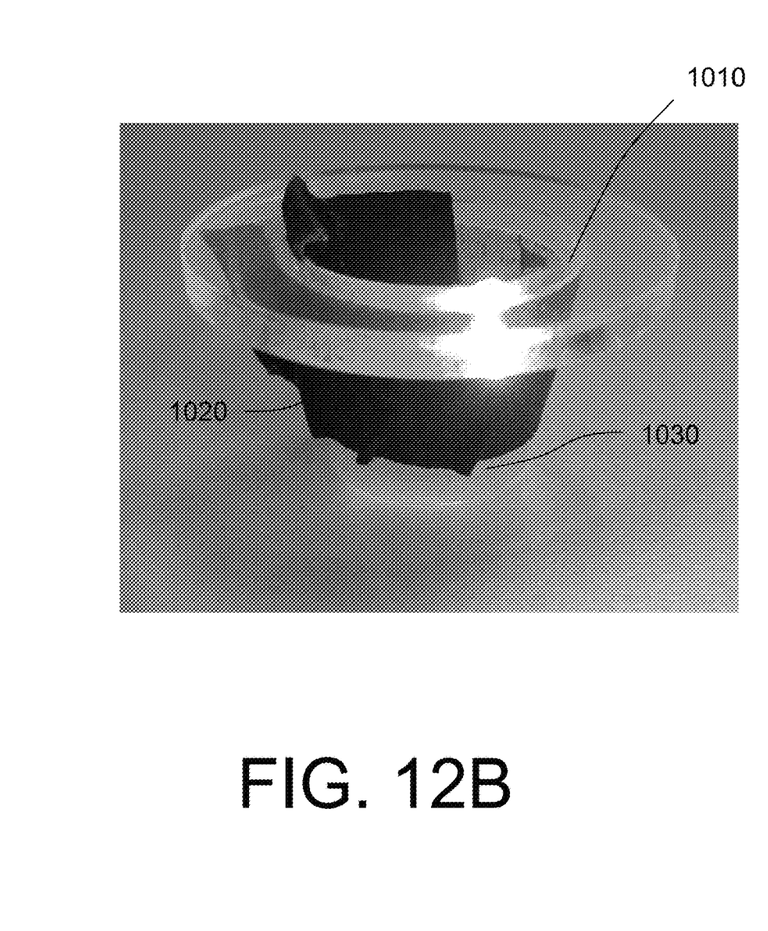
FIG. 12B illustrates a second example of an illumination condition of an example embodiment of a light guiding structure of a patient interface device.

FIG. 12A illustrates a first example of an illumination condition of an example embodiment of light guiding structure 1000 of a patient interface device, and FIG. 12B illustrates a second example of an illumination condition of light guiding structure 1000 of a patient interface device (e.g., patient interface device 300).

In particular, as shown in FIG. 12A, when the light (e.g., laser light) impinges on light receiving interface or surface 1010 of light guiding structure 1000 at some angles, the light is passed via total internal reflection to the diffusing light-emitting interface or surface 1030, and thus diffusely provided in the vicinity of patient's eye 5. On the other hand, when the light (e.g., laser light) impinges on light receiving interface or surface 1010 of light guiding structure 1000 at other angles, the light is not totally internally reflected by light guiding structure 1000 to diffusing light-emitting interface or surface 1030. Nevertheless, some light still emerges at diffusing light-emitting interface or surface 1030.

Figure 13:
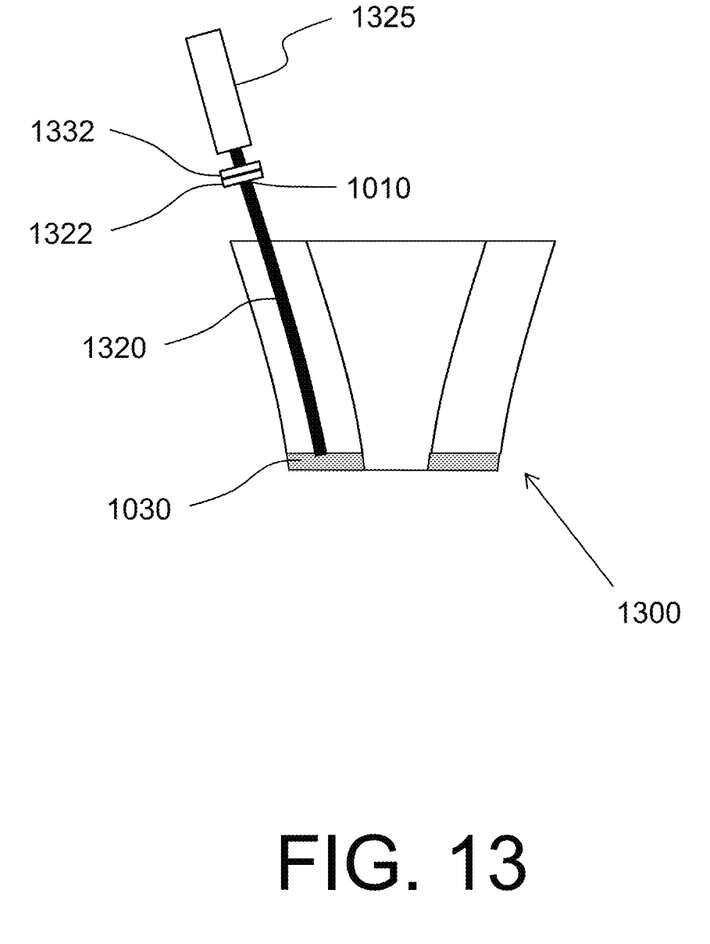
FIG. 13 illustrates a portion of another example embodiment of a light guiding structure of a patient interface device.

FIG. 13 illustrates a portion of another example embodiment of a light guiding structure 1330 of a patient interface device (e.g., patient interface device 300).

Here, light guiding structure 1300 comprises one or more optical fibers 1320, for example attached to an interior of embedded in a shell (e.g., shell 310) of a patient interface device (e.g., patient interface device 300). Here optical fiber 1320 is embedded in a frustoconical structure and interfaces at a first end thereof to a laser 1325 via a connector pair 1322/1332 to receive laser light at light receiving interface or surface 1010. At a second end, optical fiber 1320 couples the light to light-emitting interface or surface 1030 (which may be light diffusive), as described before. In this case, other than optical fiber 1320 and light-emitting interface or surface 1030, light guiding structure 1100 need not comprise a material which is transparent to visible light.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A patient interface device, comprising:
a shell defining a chamber therein;
a first interface port configured to be interfaced with a patient's eye, the first interface port being disposed at a first side of the shell and including an applanating lens for application to the patient's eye during a laser surgery procedure and a flexible or semi-flexible membrane on which the applanating lens is provided, the membrane having through channels extending through the membrane from the chamber above the applanating lens to a space below the applanating lens;
a second interface port disposed at a second side of the shell which is opposite the first side of the shell and which is configured to be interfaced with a laser surgery apparatus-when; and
a light guiding structure having at a first end thereof a light receiving interface, configured to receive light, and having at a second end thereof a light-diffusing, light-emitting, interface, wherein the light-diffusing, light-emitting, interface is disposed adjacent the applanating lens and configured to diffusely provide the light in a vicinity of the patient's eye when the applanating lens is applied to the patient's eye.

2. The patient interface device of claim 1, wherein the light guiding structure is tubular and has a light blocking material applied to at least a portion of an interior surface thereof extending from the first end to the second end, and further has the light blocking material applied to at least a portion of an exterior surface thereof extending from the first end to the second end.

3. The patient interface device of claim 2, wherein the light blocking material comprises a black material.

4. The patient interface device of claim 1, wherein the light guiding structure has a shape of a hollow conical frustum.

5. The patient interface device of claim 1, wherein the light guiding structure comprises at least one optical fiber.

6. The patient interface device of claim 1, wherein the applanating lens has formed therein a circumferential groove, and wherein the membrane includes a portion extending into the circumferential groove of the applanating lens to fix the applanating lens to the membrane.

7. The patient interface device of claim 1, wherein the membrane has formed therein a plurality of support structures configured to support the membrane on a sclera of the patient's eye when the applanating lens is applied to the patient's eye.

8. The patient interface device of claim 1, wherein the light guiding structure is configured to internally reflect light from walls thereof from the light receiving interface to the light-emitting interface.

9. The patient interface device of claim 1, wherein surfaces of the light guiding structure are polished to a first degree, except a surface of the light-diffusing, light-emitting, interface which is polished to a second degree which is less than the first degree such that the surface of the light-diffusing, light-emitting, interface is rougher than other surfaces of the light guiding structure.

10. A system, comprising:
a laser surgery apparatus, comprising: a laser source,
a lens assembly configured to direct laser light from the laser source to a target area of a patient's eye for laser surgery,
a docking receptacle, and
an illuminating light source; and
a patient interface device, comprising:
   a shell, defining a chamber within the shell,
   a first interface port configured to be interfaced with the patient's eye, the first interface port being disposed at a first side of the shell and including an applanating lens for application to the patient's eye during a laser surgery procedure and a flexible or semi-flexible membrane on which the applanating lens is provided, the membrane having through channels extending through the membrane from the chamber above the applanating lens to a space below the applanating lens,
   a second interface port disposed at a second side of the shell which is opposite the first side of the shell and which is configured to be interfaced with the docking receptacle, and
   a light guiding structure having at a first end thereof a light receiving interface, configured to receive light from the illuminating light source, and having at a second end thereof a light-diffusing, light-emitting, interface, wherein the light-diffusing, light-emitting, interface is disposed adjacent the applanating lens and configured to diffusely provide the light in a vicinity of the patient's eye when the applanating lens is applied to the patient's eye.

11. The system of claim 10, further comprising an imaging device configured to produce image data for the patient's eye while the patient's eye is illuminated by the light from the light guiding structure.

12. The system of claim 10, wherein the light guiding structure is tubular and has a light blocking material applied to at least a portion of an interior surface thereof extending from the first end to the second end, and further has the light blocking material applied to at least a portion of an exterior surface thereof extending from the first end to the second end.

13. The system of claim 12, wherein the light blocking material comprises a black material.

14. The system of claim 10, wherein the light guiding structure comprises at least one optical fiber.

15. The system of claim 10, wherein the applanating lens has formed therein a circumferential groove, and wherein the flexible membrane includes a portion extending into the circumferential groove of the applanating lens to fix the applanating lens to the membrane.

16. The system of claim 10, wherein the light guiding structure is configured to internally reflect light from walls thereof from the light receiving interface to the light-emitting interface.

17. The system of claim 10, wherein the membrane has formed therein a plurality of support structures configured to support the membrane on a sclera of the patient's eye when the applanating lens is applied to the patient's eye.

* * * * *